United States Patent [19]

Suvorov et al.

[11] 3,993,690

[45] Nov. 23, 1976

[54] METHOD OF OBTAINING AROMATIC TRI-OR-TETRACARBOXYLIC ACIDS

[76] Inventors: Boris Viktorovich Suvorov, ulitsa Pushkina, 102/44, kv. 27; Dauren Khamitovich Sembaev, ulitsa Furmanova, 91/97, kv. 7; Ivetta Sergeevna Kolodina, 7 Mikroraion, 36, kv. 18; Lidia Anatolievna Stepanova, ulitsa Pavlova, 16, all of Alma-Ata, U.S.S.R.

[22] Filed: Dec. 22, 1975

[21] Appl. No.: 643,111

Related U.S. Application Data

[63] Continuation of Ser. No. 22,050, March 23, 1970, abandoned.

[30] Foreign Application Priority Data

Mar. 25, 1969 U.S.S.R. .............................. 1313364

[52] U.S. Cl. ........................ 260/524 R; 260/465 C
[51] Int. Cl.$^2$ ......................................... C07C 51/42
[58] Field of Search ..................... 260/524 R, 465 C

[56] References Cited
UNITED STATES PATENTS

| | | | |
|---|---|---|---|
| 2,499,055 | 2/1950 | Cosby et al. | 260/524 |
| 3,393,220 | 7/1968 | Winnick et al. | 260/524 |

*Primary Examiner*—James O. Thomas, Jr.
*Assistant Examiner*—A. Siegel
*Attorney, Agent, or Firm*—Holman & Stern

[57] ABSTRACT

A method of obtaining aromatic tri- or tetracarboxylic acids characterized in that tri- or tetraalkylbenzenes or the derivatives thereof with a heteroatom in the side chain, are oxidized by oxygen or an oxygen-containing gas in the vapor phase in the presence of ammonia and water vapor at a molar ratio of the parent alkylbenzenes, oxygen or oxygen-containing gas, ammonia and water vapor equal to 1:2–100:5–40:-30–100, respectively, on catalysts comprising vanadium oxides modified by the oxides of tin, titanium, bismuth or molybdenum at a molar ratio of vanadium oxides to the modifying oxides equal to 1:0.5–8 and a temperature of from 350° to 440° C, whereupon the resulting nitriles, imides, cyanimides or the mixtures thereof are subjected to acid or alkaline hydrolysis by 2–10 per cent aqueous solutions of acids or alkalis at a temperature of from 60° to 100° C.

Aromatic tri- or tetracarboxylic acids obtained by the herein-disclosed technique feature a high degree of purity and are applicable as intermediate products of organic synthesis, in particular, as parent substances for polymeric materials.

4 Claims, No Drawings

METHOD OF OBTAINING AROMATIC TRI-OR-TETRACARBOXYLIC ACIDS

This is a continuation of application Ser. No. 22,050, filed Mar. 23, 1970, now abandoned.

The invention relates to the synthesis of polyfunctional compounds, viz., aromatic tri- or tetracarboxylic acids used as intermediate products of organic synthesis, in particular, as parent compounds for polymeric substances.

Known in the prior art are methods of obtaining aromatic tri- or tetracarboxylic acids by catalytic oxidation of respective tri- and tetraalkylbenzenes in the liquid phase by molecular oxygen, as well as methods based upon the oxidation of said alkylbenzenes by potassium permanganate and nitric acid (cf. USSR Author's certificate No. 201375; U.S. Pat. No. 3,009,953).

Said methods suffer from essential disadvantages and are of no avail from the engineering viewpoint since they involve the use of catalysts which are not readily available (such as elementary bromine, ammonium bromide) and oxidants, and require expensive corrosion-resistant equipment and apparatus to effect.

The processes of direct contact oxidation in the vapour phase are inapplicable for the synthesis of aromatic tricarboxylic acids since in this case the reaction proceeds too deeply and terminates in the formation of carbon oxides. The reaction of vapour-phase catalytic oxidation is used but for synthesis of the dianhydride of pyromellitic acid from 1,2,4,5-tetramethylbenzene (cf. U.S. Pat. Nos. 2,509,855 and 2,626,566; USSR Author's certificate No. 165704), from triisopropyltoluene (USSR Author's certificate No. 185893), or from ethyltriiso-, diethyldiiso- and tetraisopropylbenzenes (USSR Author's certificate No. 189419), as well as from some oxygen-containing tetraalkylbenzenes (derivatives of alkylbenzenes with a heteroatom in side chain). This method is unfavourable due to formation of a considerable amount of impurities hardly amenable to separation.

It is an object of the present invention to develop an economic method of obtaining tri- or tetracarboxylic acids based upon oxidation of tri- or tetraalkylbenzenes or their derivatives with a heteroatom in the side chain, which would ensure the obtaining of specific products at higher level of purity and at a higher yield as compared with the methods hitherto employed.

In keeping with said and other objects the invention resides in the fact that oxidation is effected by oxygen or by an oxygen-containing gas in vapour phase in the presence of ammonia and water vapour, at a molar ratio of parent alkyl-benzenes, oxygen or oxygen-containing gas, ammonia and water vapour equal to 1:20–100:5–40:30–100, respectively, on catalysts comprising vanadium oxides modified by the oxides of tin, titanium, bismuth or molybdenum at a molar ratio of the vanadium oxides to the modifying oxides equal to 1:0.5–8, at a temperature of from 350° to 440° C. Resulting nitriles, imides, cyanimides or the mixtures thereof are subjected to acid or alkaline hydrolysis by processing with 2–10 per-cent aqueous solutions of acids or alkalis at 60°–100° C.

The herein-disclosed method of obtaining aromatic tri- or tetracarboxylic acids features the following advantages:

1. High yield percentage of specific products amounting up to 85 of the theoretical yield as referred to the parent substance;
2. High degree of purity of specific products;
3. Use of easily available oxidants, i.e. oxygen or oxygen-containing gas;
4. Dispensing with critically-short reagents such as glacial acetic acid or compounds of bromine and cobalt;
5. Use of standard commercial equipment and apparatus for the method to carry out.

The herein-offered method of obtaining aromatic tri- or tetracarboxylic acids is carried into effect as follows.

Tri- or tetraalkylbenzenes or the derivatives thereof with heteroatom in the side chain, mixed with water vapour, oxygen or oxygen-containing gas and ammonia, are passed through the catalyst bed. The parent substances, i.e., hydrocarbon, water, oxidant and ammonia are to be taken at a molar ratio of 1:30–100:20–100:5–40. The temperature within the reaction zone is to be kept at 350°–440° C. The said oxidation process proceeds in a single-tube reactor of the flow type.

Use is made of vanadium oxides modified with the oxides of tin, titanium, bismuth, molybdenum, as catalysts, the molar ratio between the vanadium oxides and modifying oxides being equal to 1:0.5–8.

Of great importance in said process of oxydative ammonolysis is the concentration of vapours of water and ammonia which determines the selectivity of catalytic conversion of the parent compounds into nitriles, imides, cyanimides having the initial number of substituents and alpha-carbon atom with an aromatic cycle.

The thus-obtained nitrogen-containing products (nitriles, imides, cyanimides) are subjected to hydrolysis. The reaction of hydrolysis is effected by a 2–10 per-cent solution of acid or alkali at a temperature of 60°–100° C in glass vessels or stainless-steel reservoirs. As a hydrolyst use can be made of, say, sodium or potassium hydroxide, sulphuric acid or hydrochloric acid.

The synthetized specific product (tri- or tetracarboxylic acid is extracted by the conventional method, consisting in that the obtained solution is evaporated, cooled down, the precipitated specific product is washed with cold water and filtered off.

To give a clearer idea of the present invention given below are some examples of obtaining tri- or tetracarboxylic acids by the method of the invention.

EXAMPLE 1

The process runs in the flow-type apparatus with a stainless-steel reaction tube dia. 20 mm and 1200 mm long. Vanadium-titanium catalyst (molar ratio of oxides $V_2O_5: TiO_2=1:05$) is charged into the reactor in an amount of 70 ml. The mixture of reagents composed of 1,2,4-trimethylbenzene (pseudocumene), water, air and ammonia is fed into the reactor at 420° C, the rate of feed of pseudocumene being 38.7 g, water, 190 g, air, 1700 lit., ammonia, 82.5 g per liter of catalyst per hour, the duration of the experiment equalling 10 hours. The total amount of pseudocumene fed throughout the reaction is 27 g.

Reaction products are caught in a cyclone with a water film, the cyclone being washed with a 2-per-cent aqueous solution of sulphuric acid.

The solid reaction product is filtered out and washed by benzene. According to IR-spectroscopy and elementary analysis data the reaction product obtained is found to correspond to 4-cyanphthalimide, its melting point lying at 238° C.

Actual percentage of constituents: C, 62.80; H, 2.34; N, 16.06. $C_9H_4O_2N_2$. Calculated percentage of constituents: C, 62.79; H, 2.34; N, 16.25.

The total yield of 23.3 g of 4-cyanphthalimide is 60.2 per cent of the theoretical yield as referred to the amount of pseudocumene fed throughout the reaction process.

Further, 4-cyanphthalimide is hydrolyzed by processing with a 2-per-cent aqueous solution of sodium hydroxide while boiling. When under hydrolysis 4-cyanphthalimide (as per the data of polarographic analysis) is found to convert by 99.5 per cent into trimellitic acid. The latter is separated as follows: the hydrolysis having been completed, the alkaline solution is acidulated, concentrated under vacuum (residual pressure 10 mm Hg) and cooled down to 1° C. The precipitated trimellitic acid is filtered out, washed by cold water and dried. Washings are added to filtrate, the resulting solution is concentrated, cooled and trimellitic acid is refiltered out. After having been recrystallized from water trimellitic acid is found to melt at 229° C and to have neutralization equivalent equal to 70.0 which is well consistent with the estimated value.

After the solid substance has been separated from the solution of the catalytic reaction products, said solution in an amount of 1000 ml, is alkaline-hydrolyzed adding 50 g of solid sodium hydroxide thereto. Then the hydrolyzate is acidulated, cooled down to room temperature and filtered out from precipitated methylterephthalic and methylisophthalic acids. The filtrate is concentrated and cooled down to 1° C, trimellitic acid being precipitated. The precipitate is filtered out, washed by cooled water and dried. The amount of 9.5 g trimellitic acid with melting point at 229° C and neutralization equivalent of 70.1 is separated.

The total amount of 36.7 g of trimellitic acid is separated which makes up 77.5 per cent of the theoretical yield as referred to the amount of pseudocumene fed into the reactor.

EXAMPLE 2

A test is conducted on a catalyst sample similar to that of Example 1. The mixture of pseudocumene, air, ammonia and water is fed into the reactor at 390° C, the rate of feed of pseudocumene being 38.7 g, water, 450 g air, 1700 lit and ammonia, 164 g per liter of catalyst per hour, the duration of the experiment being 10 hours. The total amount of pseudocumene fed is 27 g.

The catching and analysis technique of the reaction products is similar to that described in Example 1.

9.3 g of 4-cyanphthalimide is obtained in terms of a solid reaction product that makes up 24.2 per cent of the theoretical yield as referred to the amount of pseudocumene fed into the reactor. The 4-cyanphthalimide obtained is subjected to hydrolysis by a 2-per cent aqueous solution of sodium hydroxide at 80° C.

The hydrolizate is acidulated, cooled down to room temperature and filtered out to obtain 10.6 g of trimellitic acid. Hydrolysis of the aqueous solution of hydrolizate is effected by resorting to the same technique as in Example 1, 27.7 g of trimellitic acid resulting therefrom.

The total amount of the trimellitic acid is 38.3 g which makes up 81% of theoretical yield as referred to the amount of pseudocumene fed into the reactor.

EXAMPLE 3

The experiment conditions with pseudocumene are similar to those described in Example 2. The mixture of $V_2O_5$ and $TiO_2$ taken at a ratio of 1:8 is used a catalyst.

The reaction products effluent from the reaction tube are caught by two successively mounted scrubbers, washed by hot per-cent aqueous solution of sodium hydroxide. After finishing the experiment the alkaline solution is boiled till the completion of the reaction products hydrolysis. After acidification of hydrolysate the water- insoluble methyltere- and methylisophthalic acids are precipitated, which trimellitic acid remains in the solution. To separate the latter the filtrate is evaporated under vacuum (residual pressure 10 mm Hg) and cooled down to 1° C, whereupon trimellitic acid is precipitated. The total amount of trimellitic acid obtained is 402 g which makes up 85 per cent of the theoretical yield as referred to the amount of pseudocumene used for the reaction.

After recrystallization from water the resulting trimellitic acid has its melting point lying at 229° C and a neutralization equivalent equal to 70.0

EXAMPLE 4

The mixture of components consisting of 1-chloromethyl-3,4-dimethylbenzene, air ammonia and water is fed into the reactor described in Example 1, onto vanadium-titanium catalyst the molar ration of $V_2O_5$:$TiO_2$ being 1:4). The temperature of the contact zone is 400° C. The rate of feed of 1-chloromethyl-3,4-dimethylbenzene — 42.8 g, water — 450 g air, 1700 lit and ammonia 164 g per liter of catalyst per hour, the duration of the experiment being 10 hours. The total of 1-chloromethyl-3,4-dimethylbenzene fed is 30 g.

The catching and analysis technique of the reaction products is similar to that described in Example 1.

25 g of 4-cyanphthalimide is obtained in terms of a solid reaction product that makes up 75 per cent of the theoretical yield as referred to the amount of 1-chloromethyl-3,4-dimethylbenzene fed into the reactor. Hydrolysis of this product effected by a 5 per cent aqueous solution of potassium hydroxide when boiling the mixture, gives 30.5 g of the trimellitic acid, which is separated by the similar way as in Example 1.

Hydrolysis of the water portion of the catalyst effected similar to the above-described, gives in addition 4.1 g of the trimellitic acid.

The total amount of the trimellitic acid is 34.6 g which makes up 85 per cent of the theoretical yield as referred to the amount of the raw material fed into the reactor.

EXAMPLE 5

The melted titanium vanadate (a molar ration of $V_2O_5$: :$TiO_2$ being 1:0.5) is charged into the reactor with a stainless steel reactor tube having the diameter 22 mm and the length 700 mm. Durol (1,2,4,5-tetramethylbenzene) is passed through the catalyst bed at a rate of 70 g per liter of catalyst per hour. The water vapour, ammonia and air are simultaneously fed into the reactor in the amount of 470 g, 120 g and 1600 lit per liter of catalyst per hour, respectively. The temperature in the contact zone is 400° C. The duration of the experiment being 10 hours. The total amount of durol passed through the catalyst bed is 26 g.

The reaction products are catched in cyclones with a water film. Washing of the cyclone is carried out by a 1 per cent sulphuric acid aqueous solution.

The solid reaction product is separated by filtration and washed by benzene in order to remove the uncreated durol. The results of the IR-spectroscopy classify the obtained product to correspond to diimide of pyromellitic acid.

$C_{10}H_4O_4N_2$: Actual percentage of constituents: C, 56.28; H, 1.78; N, 12.74. Calculated percentage of constituents: C, 55.55; H, 1.85; N, 12.96;

The total amount of pyromellitediimide is 23.05 g which corresponds to 55 per cent of the theoretical yield referred to the amount of the raw material used for the reaction.

The resulting diimide is subjected to hydrolysis by 5 per cent aqueous solution of potassium hydroxide during 3 hours at the mixture boiling point. The solution is neutralized by hydrochloric acid and cooled down to 1° C. The precipitated crystalline pyromellitic acid is filtered out and washed by cooled water. After drying the product is found to have its melting point at 274° C and the neutralization equivalent equal to 63.4.

$C_{10}H_6O_8$: Actual percentage of constituents: C, 47.19; H, 2.29. Calculated percentage of constituents: C, 47.24; H, 2.36

Polarographic analysis finds pyromellitic acid obtained to contain no impurities of phthalic or maleic acids.

The total quantity of pyromellitic acid is 21.9 g which makes up 52 per cent of the theoretical yield as referred to the amount of durol passed through the catalyst bed.

EXAMPLE 6

The catalyst and the apparatus are similar to those used in Example 3. The mixture of durol, water, air and ammonia is fed into the reactor, the rates of feed being as follows: durol — 70 g, water — 355 g, air 16000 lit and ammonia — 300 g per liter of catalyst per hour, the reaction temperature being 440° C, the test duration 20 hours and the amount of durol fed 52 g.

The reaction products are caught in a cyclone with a water film, washing of cyclones being carried out by a 5 per cent aqueous solution of sodium hydroxide. To complete the hydrolysis process the resulting alkaline solution is boiled during 2 hours whereupon hydrolizate is acidulated, cooled down to room temperature and filtered out to obtain pyromellitic acid. According to the polarographic analysis data the specific product is found to contain no phthalic or maleic acids. After having been dried the obtained pyromellitic acid features its melting point at 274° C and the neutralization equivalent equal to 63.5.

$C_{10}H_6O_8$: Actual percentage of constituents: C, 47.32; H, 2.40. Calculated percentage of constituents: C, 47.24; H, 2.36.

The total amount of pyromellitic acid is 64.1 which makes up 65 per cent of the theoretical yield as referred to the amount of durol used for the reaction.

EXAMPLE 7

Vanadium-tin catalyst taken at a molar ration of $V_2O_5$: :$SnO_2$ = 1.05, is charge into the reactor with a stainless steel reaction tube 20 mm and 1000 mm long. Duryleneglycol is passed through the catalyst bed at 400° C aid a feed rate of 100 g per liter of catalyst per hour, water, air and ammonia being simultaneously fed into the reactor in the amount of 420 g, 14000 lit and 300 g per liter of catalyst per hour, respectively. The total amount of duryleneglycol is 30 g.

Catching of the reaction products is made in cyclones washed by a 2 per cent sulphuric acid aqueous solution. To complete the process of acid hydrolysis the reaction products are boiled during 2 hours, whereupon hydrolizate is cooled down to 1° C and pyromellitic acid is filtered out.

The pyromellitic acid obtained is found to contain no impurities of phthalic or maleic acids its physicochemical indices being similar to those of a pure acid. The total amount of pyromellitic acid is 25.7 g, its yield being 65 per cent of the theoretical one as referred to the amount of duryleneglycol passed through the catalyst bed.

Though the present invention is described in connection with the preferred embodiment thereof, it should be understood, however, that various changes and modifications may be made without departing from the spirit and scope of the invention, as those skilled in the art will easily understand. Such changes and modifications should be considered as falling within the true spirit and scope of the invention as defined in the claims to follow.

What is claimed is:

1. A method for the preparation of aromatic tri- or tetracarboxylic acids comprising oxidizing, in the vapor-phase, alkyl benzenes selected from the group consisting of trialkylbenzenes and tetraalkylbenzenes with an oxidizing agent selected from the group consisting of oxygen and oxygen-containing gases, and in the presence of ammonia and water vapor, the molar ratio of the alkylbenzene feedstock, oxidizing agent, ammonia and water vapor being 1:20–100:5–40:30–100, respectively, over catalysts comprising vanadium oxides modified with titanium oxides, the molar ratio of vanadium oxides to modifying titanium oxides being 1:0.5–8, at a temperature of from 350° to 440° C, to thereby obtain nitrogen-containing compounds selected from the group consisting of nitriles, imides, cyanimides and mixtures thereof, and hydrolyzing said nitrogen-containing compounds at a temperature of from 60° to 100° C with a 2–10% aqueous solution of a hydrolyzing agent selected from the group consisting of potassium hydroxide, sodium hydroxide, sulfuric acid and hydrochloric acid.

2. The method of claim 1, wherein the nitrogen-containing compound obtained by oxidizing the alkyl benzene is 4-cyanphthalimide.

3. The method of claim 2, wherein the alkylbenzene is 1, 2, 4-trimethylbenzene.

4. A method for the preparation of trimellitic acid comprising oxidizing, in the vapor-phase, 1-chloromethyl-3,4-dimethylbenzene with an oxidizing agent selected from the group consisting of oxygen and oxygen-containing gases, and in the presence of ammonia and water vapor, the molar ratio of the 1-chloromethyl-3,4-dimethylbenzene feedstock, oxidizing agent, ammonia and water vapor being 1:20–100- :5–40:30–100, respectively, over catalysts comprising vanadium oxides modified with titanium oxides, the molar ratio of vanadium oxides to modifying titanium oxides being 1:0.5–8, at a temperature of from 350° to 440° C, to thereby obtain nitrogen-containing compounds selected from the group consisting of nitriles, imides, cyanimides and mixtures thereof, and hydrolyzing said nitrogen-containing compounds at a temperature of from 60° to 100° C with a 2–10% aqueous solution of a hydrolyzing agent selected from the group consisting of potassium hydroxide, sodium hydroxide, sulfuric acid and hydrochloric acid.

\* \* \* \* \*